(12) United States Patent
Blann et al.

(10) Patent No.: US 7,511,183 B2
(45) Date of Patent: Mar. 31, 2009

(54) TETRAMERIZATION OF OLEFINS

(75) Inventors: Kevin Blann, Alberton (ZA); Annette Bollmann, Henley-on-Klip (ZA); John Thomas Dixon, Vanderbijlpark (ZA); Arno Neveling, Sasolburg (ZA); David Hedley Morgan, Sasolburg (ZA); Hulisani Maumela, Johannesburg (ZA); Esna Killian, Vanderbijlpark (ZA); Fiona Millicent Hess, Sasolburg (ZA); Stefanus Otto, Sasolburg (ZA); Lana Pepler, Sasolburg (ZA); Hamdani Ahmed Mahomed, Sasolburg (ZA); Matthew James Overett, Johannesburg (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 0 days.

(21) Appl. No.: 10/539,517

(22) PCT Filed: Dec. 19, 2003

(86) PCT No.: PCT/ZA03/00187

§ 371 (c)(1),
(2), (4) Date: Apr. 5, 2006

(87) PCT Pub. No.: WO2004/056479

PCT Pub. Date: Jul. 8, 2004

(65) Prior Publication Data

US 2006/0229480 A1    Oct. 12, 2006

Related U.S. Application Data

(60) Provisional application No. 60/509,309, filed on Oct. 6, 2003, provisional application No. 60/478,379, filed on Jun. 13, 2003, provisional application No. 60/435,405, filed on Dec. 20, 2002.

(30) Foreign Application Priority Data

| Dec. 20, 2002 | (ZA) | ................................ 2002/10339 |
| Jun. 13, 2003 | (ZA) | ................................ 2003/4632 |
| Oct. 6, 2003 | (ZA) | ................................ 2003/7774 |

(51) Int. Cl.
| C07C 2/08 | (2006.01) |
| C07C 2/32 | (2006.01) |
| C07C 2/36 | (2006.01) |
| B01J 31/18 | (2006.01) |
| B01J 31/24 | (2006.01) |

(52) U.S. Cl. ........................ 585/513; 585/527; 502/103; 502/121; 502/122; 502/123; 502/125

(58) Field of Classification Search ................. 585/513, 585/527; 502/103, 121, 122, 123, 125
See application file for complete search history.

(56) References Cited

U.S. PATENT DOCUMENTS

| 2,699,457 | A | 1/1955 | Ziegler et al. |
| 3,635,937 | A | 1/1972 | Bauer et al. |
| 3,676,523 | A | 7/1972 | Mason |
| 3,906,053 | A | 9/1975 | Lanier |
| 4,628,138 | A | 12/1986 | Barnett et al. |
| 6,184,428 | B1 | 2/2001 | Zahoor et al. |
| 7,022,788 | B2 * | 4/2006 | Wass ........................... 526/172 |

FOREIGN PATENT DOCUMENTS

| DE | 1 443 927 | | 10/1962 |
| JP | 07215896 A | * | 8/1995 |
| WO | WO 01/10876 | * | 2/2001 |
| WO | WO 02/04119 A1 | | 1/2002 |
| WO | WO 03/053891 A1 | | 7/2003 |

OTHER PUBLICATIONS

Carter, et al., "High Activity Ethylene Trimerisation Catalysts Based on Diphosphine Ligands", Chemical Communication, vol. 2002, No. 8, XP002277009, pp. 858-859, (Mar. 20, 2002).

* cited by examiner

*Primary Examiner*—Caixia Lu
(74) *Attorney, Agent, or Firm*—Finnegan, Henderson, Farabow, Garrett, & Dunner, L.L.P.

(57) ABSTRACT

The invention describes a process for tetramerisation of olefins wherein the product stream of the process contains more than 30% of the tetramer olefin. The process includes the step of contacting an olefinic feedstream with a catalyst system containing a transition metal compound and a heteroatomic ligand.

38 Claims, 1 Drawing Sheet

Fig. 1

TETRAMERIZATION OF OLEFINS

CROSS REFERENCE TO RELATED APPLICATIONS

This application is a National Phase application based on PCT/ZA2003/000187, filed on Dec. 19, 2003, the contents of which are incorporated herein by reference and claims the priority of South African Application No. 2002/10339, filed on Dec. 20, 2002, South African Application No. 2003/4632, filed on Jun. 13, 2003, South African Application No. 2003/7774, filed on Oct. 6, 2003, and claims the benefit of U.S. Provisional Application No. 60/435,405, filed on Dec. 20, 2002, U.S. Provisional Application No. 60/478,379, filed on Jun. 13, 2003, and U.S. Provisional Application No. 60/509,309, filed on Oct. 6, 2003, the contents of each of which are incorporated herein by reference.

FIELD OF THE INVENTION

This invention relates to an olefin tetramerisation process, a catalyst system for tetramerisation of olefins and the identification and use of ligands for a catalyst system for tetramerisation of olefins.

BACKGROUND OF THE INVENTION

This invention defines a process and catalyst system that facilitates the production of 1-octene in high selectivity, while avoiding the co-production of significant quantities of butenes, other octene isomers, specific higher oligomers and polyethylene. The catalyst system can also be used for the tetramerisation of other olefins, especially α (alpha)-olefins.

Despite the well known value of 1-octene, the art does not teach a commercially successful process for the tetramerisation of ethylene to produce 1-octene selectively. Conventional ethylene oligomerisation technologies produce a range of α-olefins following either a Schulz-Flory or Poisson product distribution. By definition, these mathematical distributions limit the mass % of the tetramer that can be formed and make a distribution of products. In this regard, it is known from prior art (U.S. Pat. No. 6,184,428) that a nickel catalyst comprising a chelating ligand, preferably 2-diphenyl phosphino benzoic acid (DPPBA), a nickel precursor, preferably $NiCl_2.6H_2O$, and a catalyst activator, preferably sodium tetraphenylborate, catalyse the oligomerisation of ethylene to yield a mixture of linear olefins containing 1-octene. The selectivity towards linear $C_8$ α-olefins is claimed to be 19%. Similarly the Shell Higher Olefins Process (SHOP process, U.S. Pat. Nos. 3,676,523 and 3,635,937) using a similar catalyst system is reported to typically yield 11 mass % 1-octene in its product mixture (Chem Systems PERP reports 90-1, 93-6 and 94/95S12).

Ziegler-type technologies based on trialkylaluminium catalysts, independently developed by Gulf Oil Chemicals Company (Chevron, e.g. DE patent 1,443,927) and Ethyl Corporation (BP/Amoco, e.g. U.S. Pat. No. 3,906,053), are also commercially used to oligomerise ethylene to mixtures of olefins that reportedly contain 13-25 mass % 1-octene (Chem Systems PERP reports 90-1, 93-6, and 94/95S12).

The prior art also teaches that chromium-based catalysts containing heteroatomic ligands with both phosphorus and nitrogen heteroatoms selectively catalyse the trimerisation of ethylene to 1-hexene. Examples of such heteroatomic ligands for ethylene trimerisation include bis(2-diethylphosphino-ethyl) amine (WO 03/053891, hereby fully incorporated herein by means of reference) as well as (o-methoxyphenyl)$_2$PN(methyl)P(o-methoxyphenyl)$_2$ (WO 02/04119, hereby fully incorporated herein by means of reference). Both these catalyst systems and processes are very specific for the production of 1-hexene and only yield 1-octene as an impurity (typically less than 3 mass % of the product mixture as disclosed by WO 02/04119). The coordinating phosphorus hetero atoms in (o-methoxyphenyl)$_2$PN(methyl)P(o-methoxyphenyl)$_2$ (WO 02/04119) are spaced apart by one nitrogen atom. It is believed that the nitrogen atom does not coordinate with the chromium, at least in the absence of an activator, and that without any further electron donating atoms on the ligand it is a bidentate system. Furthermore it is argued that the polar, or electron donating substituents in the ortho-position of the phenyl groups help form a tridentate system, which is generally believed to enhance selectivity towards 1-hexene formation (see *Chem. Commun.,* 2002, 858-859: "This has lead us to hypothesise that the potential for ortho-methoxy groups to act as pendent donors and increase the coordinative saturation of the chromium centre is an important factor.") WO 02/04119 (Example 16) teaches the production of octenes using a trimerisation of olefins process and catalyst system. In this instance, 1-butene was co-trimerised with two ethylene molecules to give 30% octenes. However, the nature of these octenes was not disclosed and the applicant believes that they consist of a mixture of linear and branched octenes.

The prior art teaches that high 1-octene selectivities cannot be achieved since expansion of the generally accepted seven-membered metallacycle reaction intermediate for ethylene trimerisation (*Chem. Commun.,* 1989, 674) to a nine-membered metallacyle is unlikely to occur (*Organometallics,* 2003, 22, 2564; *Angew. Chem. Int. Ed.,* 2003, 42 (7), 808). It is argued that the nine-membered ring is the least favoured medium-sized ring and should thus be disfavoured relative to the seven-membered ring (*Organometallics,* 2003, 22, 2564). In addition, it is also stated by the same authors that, "if a nine-membered ring formed, it would be more likely to grow to an eleven- or thirteen-membered ring. In other words, one would never expect much octene, but formation of some (linear) decene or dodecene would be more reasonable."

Despite the teaching of the opposite, the applicant has now found a process for selectively producing a tetramerised olefin. The applicant has further found that chromium-based catalysts containing mixed heteroatomic ligands with both nitrogen and phosphorus heteroatoms, without any polar substituents on the hydrocarbyl or heterohydrocarbyl groups on the phosphorus atom, can be used to selectively tetramerise ethylene to 1-octene often in excess of 70 mass % selectivity. This high 1-octene selectivity cannot be achieved via conventional one-step ethylene oligomerisation or trimerisation technologies which at most yield 25 mass % 1-octene.

SUMMARY OF THE INVENTION

This invention relates to a process for selectively producing tetrameric products.

This invention specifically relates to a process for selectively producing tetrameric products such as 1-octene from olefins such as ethylene.

The invention relates to a process for selectively producing tetrametric products using a transition metal catalyst system containing a heteroatomic ligand.

According to a first aspect of the invention there is provided a process for tetramerisation of olefins wherein the product of the tetramerisation process is an olefin and makes up more than 30% of the product stream of the process.

According to a second aspect of the invention the tetramerisation process includes the step of contacting an olefinic feedstream with a catalyst system which includes a transition metal and a heteroatomic ligand and wherein the product of the tetramerisation process is an olefin and makes up more than 30% of the product stream of the process.

In this specification, % will be understood to be a mass %.

The term "tetramerisation" generally refers to the reaction of four, and preferably four identical, olefinic monomer units to yield a linear and/or branched olefin.

By heteroatomic is meant a ligand that contains at least two heteroatoms, which can be the same or different, where the heteroatoms may be selected from phosphorus, arsenic, antimony, sulphur, oxygen, bismuth, selenium or nitrogen.

The feedstream will be understood to include an olefin to be tetramerised and can be introduced into the process according to the invention in a continuous or batch fashion.

The product stream will be understood to include a tetramer, which tetramer is produced according to the invention in a continuous or batch fashion.

The feedstream may include an α-olefin and the product stream may include at least 30%, preferably at least 35%, of a tetramerised α-olefin monomer.

The process may include a process for tetramerisation of α-olefins. Under the term α-olefins is meant all hydrocarbon compounds with terminal double bonds. This definition includes ethylene, propylene, 1-butene, isobutylene, 1-pentene, 1-hexene, 1-octene and the like.

The process may include a process for tetramerisation of α-olefins to selectively yield tetrameric α-olefin products.

The olefinic feedstream may include ethylene and the product stream may include at least 30% 1-octene. The process may be a process for tetramerisation of ethylene.

The invention allows the ligand, catalyst system and/or process conditions to be selected to give a product stream of more than 40%, 50%, 60% or 70% α-olefins. It may be preferable, depending on the further use of the product stream, to have such high selectivities of the α-olefin.

The olefinic feedstream may include ethylene and the ($C_6$+$C_8$): ($C_4$+$C_{10}$) ratio in the product stream may be more than 2.5:1.

The olefinic feedstream may include ethylene and the $C_8$:$C_6$ ratio in the product stream is more than 1.

The ethylene may be contacted with the catalyst system at a pressure of preferably greater than 10 barg, more preferably greater than 30 barg.

The heteroatomic ligand may be described by the following general formula $(R)_n$A-B-C$(R)_m$ where A and C are independently selected from a group which comprises phosphorus, arsenic, antimony, oxygen, bismuth, sulphur, selenium, and nitrogen, and B is a linking group between A and C, and R is independently selected from any homo or hetero hydrocarbyl group and n and m is determined by the respective valence and oxidation state of A and/or C.

A and/or C may be a potential electron donor for coordination with the transition metal.

An electron donor is defined as that entity that donates electrons used in chemical, including dative covalent, bond, formation.

The heteroatomic ligand may be described by the following general formula $(R^1)(R^2)$A-B-C$(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently selected from hydrocarbyl or hetero hydrocarbyl or substituted hydrocarbyl or substituted hetero hydrocarbyl groups.

The heteroatomic ligand may be described by the following general formula $(R^1)(R^2)$A-B-C$(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently non-aromatic or aromatic, including hetero aromatic, groups.

Any of the groups $R^1$, $R^2$, $R^3$ and $R^4$ may independently be linked to one or more of each other or to the linking group B to form a cyclic structure together with A and C, A and B or B and C.

Any substituents on one or more of $R^1$, $R^2$, $R^3$ and $R^4$ may be not electron donating. $R^1$, $R^2$, $R^3$ and $R^4$ may independently be non aromatic or aromatic, including hetero aromatic, groups and not all the groups $R^1$, $R^2$, $R^3$ and $R^4$, if aromatic, have a substituent on the atom adjacent to the atom bound to A or C.

Each non electron donating substituent on one or more of $R^1$, $R^2$, $R^3$ and $R^4$ may be non-polar. IUPAC defines non-polar as an entity without a permanent electric dipole moment.

Suitable non-polar substituents may be a methyl, ethyl, propyl, butyl, isopropyl, isobutyl, tert-butyl, pentyl, hexyl, cyclopentyl, 2-methylcyclohexyl, cyclohexyl, cylopentadienyl, phenyl, bi-phenyl, naphthyl, tolyl, xylyl, mesityl, ethenyl, propenyl and benzyl group, or the like.

$R^1$, $R^2$, $R^3$ and $R^4$ may be independently selected from a group comprising a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group. Preferably, $R^1$, $R^2$, $R^3$ and $R^4$ may independently be selected from a group comprising a phenyl, tolyl, biphenyl, naphthyl, thiophenyl and ethyl group.

B may be selected from any one of a group comprising: organic linking groups comprising a hydrocarbylene, a substituted hydrocarbylene, a heterohydrocarbylene and a substituted heterohydrocarbylene; inorganic linking groups comprising single atom links; ionic links; and a group comprising methylene, dimethylmethylene, 1,2-ethylene, 1,2-phenylene, 1,2-propylene, 1,2-catecholate, —($CH_3$)N—N($CH_3$)—, —B($R^5$)—, —Si$(R^5)_2$, —P($R^5$)— or —N($R^5$)—, wherein $R^5$ is hydrogen, a hydrocarbyl or substituted hydrocarbyl, a substituted heteroatom or a halogen. Preferably, B may be —N($R^5$)— and $R^5$ is a hydrocarbyl or a substituted hydrocarbyl group. $R^5$ may be hydrogen or may be selected from the groups consisting of alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^5$ may be an isopropyl, a 1-cyclohexyl-ethyl, a 2-methylcyclohexyl or a 2-octyl group.

B may be selected to be a single atom spacer. A single atom linking spacer is defined as a substituted or non-substituted atom that is bound directly to A and C.

A and/or C may be independently oxidised by S, Se, N or O.

A and C may be independently phosphorus or phosphorus oxidised by S or Se or N or O.

The ligand may also contain multiple $(R)_n$A-B-C$(R)_m$ units. Not limiting examples of such ligands include dendrimeric ligands as well as ligands where the individual units are coupled either via one or more of the R groups or via the linking group B. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$ and 1,4-di-(P(phenyl)N(methyl)P(phenyl)$_2$)-benzene.

The ligands can be prepared using procedures known to one skilled in the art and procedures disclosed in published literature. Examples of ligands are: (phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-$^t$butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (((phenyl)$_2$P)$_2$NCH$_2$CH$_2$)N, (ethyl)$_2$PN(methyl)P(ethyl)$_2$, (ethyl)$_2$PN(isopropyl)P(phenyl)$_2$, (ethyl)(phenyl)PN(methyl)P(ethyl)(phenyl), (ethyl)(phenyl)PN(isopropyl)P(phenyl)$_2$, (phenyl)$_2$P(=Se)N(isopropyl)P(phenyl)$_2$, (phenyl)$_2$PCH$_2$CH$_2$P(phenyl)$_2$, (o-ethylphenyl)(phenyl)PN(isopropyl)P(phenyl)$_2$, (o-methylphenyl)$_2$PN(isopropyl)P(o-methylphenyl)(phenyl), (phenyl)$_2$PN(benzyl)P(phenyl)$_2$, (phenyl)$_2$PN(1-cyclohexyl-ethyl)P(phenyl)$_2$, (phenyl)$_2$PN[CH$_2$CH$_2$CH$_2$Si(OMe$_3$)]P(phenyl)$_2$, (phenyl)$_2$PN(cyclohexyl)P(phenyl)$_2$, phenyl)$_2$PN(2-methylcyclohexyl)P(phenyl)$_2$, (phenyl)$_2$PN(allyl)P(phenyl)$_2$, (2-naphthyl)$_2$PN(methyl)P(2-naphthyl)$_2$, (p-biphenyl)$_2$PN(methyl)P(p-biphenyl)$_2$, (p-methylphenyl)$_2$PN(methyl)P(p-methylphenyl)$_2$, (2-thiophenyl)$_2$PN(methyl)P(2-thiophenyl)$_2$, (phenyl)$_2$PN(methyl)N(methyl)P(phenyl)$_2$, (m-methylphenyl)$_2$PN(methyl)P(m-methylphenyl)$_2$, (phenyl)$_2$PN(isopropyl)P(phenyl)$_2$, and (phenyl)$_2$P(=S)N(isopropyl)P(phenyl)$_2$.

The catalyst system may include an activator and the process may include the step of combining in any order a heteroatomic ligand with a transition metal precursor and an activator.

The process may include the step of generating a heteroatomic coordination complex in situ from a transition metal precursor and a heteroatomic ligand. The process may include the step of adding a pre-formed coordination complex, prepared using a heteroatomic ligand and a transition metal precursor, to a reaction mixture, or the step of adding separately to the reactor, a heteroatomic ligand and a transition metal precursor such that a heteroatomic coordination complex of a transition metal is generated in situ. By generating a heteroatomic coordination complex in situ is meant that the complex is generated in the medium in which catalysis takes place. Typically, the heteroatomic coordination complex is generated in situ. Typically, the transition metal precursor, and heteroatomic ligand are combined (both in situ and ex situ) to provide metal/ligand ratios from about 0.01:100 to 10 000:1, and preferably, from about 0.1:1 to 10:1.

The transition metal may be selected from any one of a group comprising chromium, molybdenum, tungsten, titanium, tantalum, vanadium and zirconium, preferably chromium.

The transition metal precursor which, upon mixing with the heteroatomic ligand and an activator, catalyses ethylene tetramerisation in accordance with the invention, may be a simple inorganic or organic salt, a co-ordination or organometallic complex and may be selected from any one of a group comprising chromium trichloride tris-tetrahydrofuran complex, (benzene)tricarbonyl chromium, chromium (III) octanoate, chromium (III) acetylacetonate, chromium hexacarbonyl, and chromium (III) 2-ethylhexanoate. The preferred transition metal precursors include chromium (III) acetylacetonate and chromium (III) 2-ethylhexanoate.

The heteroatomic ligand can be modified to be attached to a polymer chain so that the resulting heteroatomic coordination complex of the transition metal is soluble at elevated temperatures, but becomes insoluble at 25° C. This approach would enable the recovery of the complex from the reaction mixture for reuse and has been used for other catalyst as described by D. E. Bergbreiter et al., *J. Am. Chem. Soc.*, 1987, 109, 177-179. In a similar vein these transition metal complexes can also be immobilised by binding the heteroatomic ligands to silica, silica gel, polysiloxane or alumina or the like backbone as, for example, demonstrated by C. Yuanyin et al., *Chinese J. React. Pol.*, 1992, 1(2), 152-159 for immobilising platinum complexes.

The activator for use in the process may in principle be any compound that generates an active catalyst when combined with the heteroatomic ligand and the transition metal precursor. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

Suitable organoaluminium compounds include compounds of the formula AlR$_3$, where each R is independently a C$_1$-C$_{12}$ alkyl, an oxygen containing moiety or a halide, and compounds such as LiAlH$_4$ and the like. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

Examples of suitable organoboron compounds are boroxines, NaBH$_4$, triethylborane, tris(pentafluoropheny)borane, tributyl borate and the like.

The activator may also be or contain a compound that acts as a reducing or oxidising agent, such as sodium or zinc metal and the like, or oxygen and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups.

The transition metal and the aluminoxane may be combined in proportions to provide Al/metal ratios from about 1:1 to 10 000:1, preferably from about 1:1 to 1000:1, and more preferably from 1:1 to 300:1.

The process may include the step of adding to the catalyst system a trialkylaluminium compound in amounts of between 0.01 to 1000 mol per mol of alkylaluminoxane.

It should be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

The process may include the step of mixing the components of the catalyst system at any temperature between −20° C. and 250° C. in the presence of an olefin. The applicant has found that the presence of an olefin may stabilise the catalyst system.

The individual components of the catalyst system described herein may be combined simultaneously or sequentially in any order, and in the presence or absence of a solvent, in order to give an active catalyst. The mixing of the catalyst components can be conducted at any temperature between −100° C. and 250° C. The presence of an olefin during the mixing of the catalyst components generally provides a protective effect which may result in improved catalyst performance. The preferred temperature range may be between 20° C. and 100° C.

The catalyst system, in accordance with the invention, or its individual components, may also be immobilised by supporting it on a support material, for example, silica, alumina, $MgCl_2$, zirconia or mixtures thereof, or on a polymer, for example polyethylene, polypropylene, polystyrene, or poly (aminostyrene). The catalyst can be formed in situ in the presence of the support material, or the support can be pre-impregnated or premixed, simultaneously or sequentially, with one or more of the catalyst components. In some cases, the support material can also act as a component of the activator. This approach would also facilitate the recovery of the catalyst from the reaction mixture for reuse. The concept was, for example, successfully demonstrated with a chromium-based ethylene trimerisation catalyst by T. Monoi and Y. Sasaki, *J. Mol. Cat. A: Chem.*, 1987, 109, 177-179. In some cases, the support can also act as a catalyst component, for example where such supports contain aluminoxane functionalities or where the support is capable of performing similar chemical functions as an aluminoxane, which is for instance the case with IOLA™ (a commercial product from Grace Davison).

The reaction products as described herein, may be prepared using the disclosed catalyst system by a homogeneous liquid phase reaction in the presence or absence of an inert solvent, and/or by slurry reaction where the catalyst system is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The process may also be carried out in an inert solvent. Any inert solvent that does not react with the activator can be used. These inert solvents may include any saturated aliphatic and unsaturated aliphatic and aromatic hydrocarbon and halogenated hydrocarbon. Typical solvents include, but are not limited to, benzene, toluene, xylene, cumene, heptane, methylcyclohexane, methylcyclopentane, cyclohexane, 1-hexene, 1-octene, ionic liquids and the like.

The process may be carried out at pressures from atmospheric to 500 barg. Ethylene pressures in the range of 10-70 barg are preferred. Particularly preferred pressures range from 30-50 barg.

The process may be carried out at temperatures from −100° C. to 250° C. Temperatures in the range of 15-130° C. are preferred. Particularly preferred temperatures range from 35-100° C.

In a preferred embodiment of the invention, the heteroatomic coordination complex and reaction conditions are selected such that the yield of 1-octene from ethylene is greater than 30 mass %, preferably greater than 35 mass %. In this regard yield refers to grams of 1-octene formed per 100 g of total reaction product formed.

In addition to 1-octene, the process may also yield different quantities of 1-butene, 1-hexene, methylcyclopentane, methylene cyclopentane, propylcyclopentane, propylene cyclopentane, specific higher oligomers and polyethylene, depending on the nature of the heteroatomic ligand and the reaction conditions. A number of these products cannot be formed via conventional ethylene oligomerisation and trimerisation technologies in the yields observed in the present invention.

Although the catalyst, its individual components, reagents, solvents and reaction products are generally employed on a once-through basis, any of these materials can, and are indeed preferred to be recycled to some extent in order to minimise production costs.

The process may be carried out in a plant which includes any type of reactor. Examples of such reactors include, but are not limited to, batch reactors, semi-batch reactors and continuous reactors. The plant may include, in combination a) a reactor, b) at least one inlet line into this reactor for olefin reactant and the catalyst system, c) effluent lines from this reactor for oligomerisation reaction products, and d) at least one separator to separate the desired oligomerisation reaction products, wherein the catalyst system may include a heteroatomic coordination complex of a transition metal precursor and an activator, as described herein.

In another embodiment of the process the reactor and a separator may be combined to facilitate the simultaneous formation of reaction products and separation of these compounds from the reactor. This process principle is commonly known as reactive distillation. When the catalyst system exhibits no solubility in the solvent or reaction products, and is fixed in the reactor so that it does not exit the reactor with the reactor product, solvent and unreacted olefin, the process principle is commonly known as catalytic distillation.

According to a further aspect of the invention, there is provided a catalyst system, as described above, for the tetramerisation of olefins. The catalyst system may include a heteroatomic ligand as described above and a transition metal. The catalyst system may also include an activator as described above.

The heteroatomic ligand is described by the following general formula $(R)_n A\text{-}B\text{-}C(R)_m$ where A and C are independently selected from a group which comprises phosphorus, arsenic, antimony, oxygen, bismuth, sulphur, selenium, and nitrogen, and B is a linking group between A and C, and R is independently selected from any homo or hetero hydrocarbyl group and n and m is determined by the respective valence and oxidation state of A and/or C.

A and/or C may be a potential electron donor for coordination with the transition metal.

The heteroatomic ligand may be described by the following general formula $(R^1)(R^2)A\text{-}B\text{-}C(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently selected from hydrocarbyl or hetero hydrocarbyl or substituted hydrocarbyl or substituted hetero hydrocarbyl groups.

The heteroatomic ligand may also be described by the following general formula $(R^1)(R^2)A\text{-}B\text{-}C(R^3)(R^4)$ where A and C are independently selected from a group which comprises phosphorus, arsenic, antimony, bismuth, and nitrogen and B is a linking group between A and C, and $R^1$, $R^2$, $R^3$ and $R^4$ are independently non-aromatic or aromatic, including hetero aromatic, groups.

Any of the groups $R^1$, $R^2$, $R^3$ and $R^4$ may independently be linked to one or more of each other or to the linking group B to form a cyclic structure together with A and C, A and B or B and C.

Any substituents on one or more of $R^1$, $R^2$, $R^3$ and $R^4$ may not be electron donating.

$R^1$, $R^2$, $R^3$ and $R^4$ may be independently non aromatic or aromatic, including hetero aromatic, groups and not all the groups $R^1$, $R^2$, $R^3$ and $R^4$, if aromatic, have a substituent on the atom adjacent to the atom bound to A or C. It appears to the applicant that single atom spacers having steric bulk promote the selectivity towards 1-octene if ethylene is tetramerised, especially if there are no substituents on the atom of the aromatic group adjacent to the atom bound to A or C. Each non electron donating substituent may be non polar. This also appears to promote selectivity towards 1-octene.

Suitable non-polar substituents may be a methyl, ethyl, propyl, butyl, isopropyl, isobutyl, tert-butyl, pentyl, hexyl, cyclopentyl, 2-methylcyclohexyl, cyclohexyl, cylopentadienyl, phenyl, bi-phenyl, naphthyl, tolyl, xylyl, mesityl, ethenyl, propenyl and benzyl group, or the like.

$R^1$, $R^2$, $R^3$ and $R^4$ may independently be selected from a group comprising a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group. Preferably, $R^1$, $R^2$, $R^3$ and $R^4$ may independently be selected from a group comprising a phenyl, tolyl, biphenyl, naphthyl, thiophenyl and ethyl group.

B may be selected from any one of a group comprising: organic linking groups comprising a hydrocarbyl, substituted hydrocarbyl, heterohydrocarbyl and a substituted heterohydrocarbyl; inorganic linking groups comprising single atom links; ionic links; and a group comprising methylene, dimethylmethylene, 1,2-ethane, 1,2-phenylene, 1,2-propane, 1,2-catechol, 1,2-dimethylhydrazine, —B($R^5$)—, —Si($R^5$)$_2$—, —P($R^5$)— and —N($R^5$)— where $R^5$ is hydrogen, a hydrocarbyl or substituted hydrocarbyl, a substituted heteroatom or a halogen. Preferably, B may be —N($R^5$)— and $R^5$ is a hydrocarbyl or a substituted hydrocarbyl group. $R^5$ may be hydrogen or may be selected from the groups consisting of alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^5$ may be an isopropyl, a 1-cyclohexylethyl, a 2-methylcyclohexyl or a 2-octyl group.

B may be selected to be a single atom spacer. The applicant has found that such a single atom spacer between A and C generally increases the selectivity of the tetramerisation catalyst.

A and/or C may be independently oxidised by S, Se, N or O. A and C may preferably be independently phosphorus or phosphorus oxidised by S or Se or N or O.

The ligand may also contain multiple $(R)_n$A-B-C$(R)_m$ units. Not limiting examples of such ligands include ligands where the individual units are coupled either via one or more of the R groups or via the linking group B. More specific, but not limiting, examples of such ligands may include 1,2-di-(N (P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$ and 1,4-di-(P(phenyl)N(methyl)P(phenyl)$_2$)-benzene.

The ligand may be selected from any one or more of a group comprising (phenyl)$_2$PN(methyl)P(phenyl)$_2$, (phenyl)$_2$PN(pentyl)P(phenyl)$_2$, (phenyl)$_2$PN(phenyl)P (phenyl)$_2$, (phenyl)$_2$PN(p-methoxyphenyl)P(phenyl)$_2$, (phenyl)$_2$PN(p-$^t$butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (((phenyl)$_2$P)$_2$NCH$_2$CH$_2$)$_2$N, (ethyl)$_2$PN(methyl)P (ethyl)$_2$, (ethyl)$_2$PN(isopropyl)P(phenyl)$_2$, (ethyl)(phenyl) PN(methyl)P(ethyl)(phenyl), (ethyl)(phenyl)PN(isopropyl) P(phenyl)$_2$, (phenyl)$_2$P(=Se)N(isopropyl)P(phenyl)$_2$, (phenyl)$_2$PCH$_2$CH$_2$P(phenyl)$_2$, (o-ethylphenyl) (phenyl)PN (isopropyl)P(phenyl)$_2$, (o-methylphenyl)$_2$PN(isopropyl)P(o-methylphenyl)(phenyl), (phenyl)$_2$PN(benzyl)P(phenyl)$_2$, (phenyl)$_2$PN(1-cyclohexyl-ethyl)P(phenyl)$_2$, (phenyl)$_2$PN [CH$_2$CH$_2$CH$_2$Si(OMe$_3$)]P(phenyl)$_2$, (phenyl)$_2$PN(cyclohexyl)P(phenyl)$_2$, phenyl)$_2$PN(2-methylcyclohexyl)P(phenyl)$_2$, (phenyl)$_2$PN(allyl)P(phenyl)$_2$, (2-naphthyl)$_2$PN (methyl)P(2-naphthyl)$_2$, (p-biphenyl)$_2$PN(methyl)P(p-biphenyl)$_2$, (p-methylphenyl)$_2$PN(methyl) P(p-methylphenyl)$_2$, (2-thiophenyl)$_2$PN(methyl)P(2-thiophenyl)$_2$, (phenyl)$_2$PN(methyl)N(methyl)P(phenyl)$_2$, (m-methylphenyl)$_2$PN(methyl)P(m-methylphenyl)$_2$, (phenyl)$_2$PN(isopropyl)P(phenyl)$_2$, and (phenyl)$_2$P(=S)N(isopropyl)P(phenyl)$_2$.

The transition metal may be selected from any one of a group comprising chromium, molybdenum, tungsten, titanium, tantalum, vanadium and zirconium, preferably chromium.

The transition metal may be derived from a transition metal precursor selected from a simple inorganic or organic salt, a co-ordination or organometallic complex and may be selected from a group comprising chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate. The preferred transition metal precursors include chromium (III) acetylacetonoate and chromium (III) 2-ethylhexanoate.

The transition metal precursor and heteroatomic ligand may have metal/ligand ratios from about 0.01:100 to 10 000:1, preferably from about 0.1:1 to 10:1.

The activator may in principle be any compound that generates an active catalyst when combined with the heteroatomic ligand and the transition metal precursor. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups. The transition metal and the aluminoxane may be in such proportions relative to each other to provide Al/metal ratios from about 1:1 to 10 000:1, preferably from about 1:1 to 1000:1, and more preferably from 1:1 to 300:1.

The catalyst system may also include a trialkylaluminium compound in amounts of between 0.01 to 100 mol per mol of aluminoxane.

According to a further aspect of the invention, there is provided a ligand, as described above, for a catalyst system, as described above, for the tetramerisation of olefins.

The invention also extends to the identification and use of ligands suitable for use in a tetramerisation of olefins process or catalyst system.

EXAMPLES OF PERFORMING THE INVENTION

The invention will now be described with reference to the following non-limiting examples. The individual components of the examples may conceivably be omitted or substituted and, although not necessarily ideal, the invention may conceivably still be performed and these components are not to be taken as essential to the working of the invention.

In the examples that follow all procedures were carried out under inert conditions, using pre-dried reagents. Chemicals were obtained from Sigma-Aldrich or Strem Chemicals unless stated otherwise. All trialkylaluminium and aluminoxane compounds and solutions thereof were obtained from Crompton Gmbh, Akzo Nobel and Albemarle Corporation. In all the examples, the molar mass of methylaluminoxane (MAO) was taken to be 58.016 g/mol, corresponding to the ($CH_3$—Al—O) unit, in order to calculate the molar quantities of MAO used in the preparation of the catalysts described in the examples below. Similarly the molar mass of ethylaluminoxane (EAO) was taken as 72.042 g/mol, corresponding to the ($CH_3CH_2$—Al—O) building block, and that of modified methylaluminoxane prepared from a 70:30 mixture of trimethylaluminium and tri-isobutylaluminium as 70.7 g/mol corresponding to the ($Me_{0.70}isonBu_{0.30}$-Al—O) unit. Ethylene oligomerisation products were analysed by GC-MS and GC-FID.

The mixed heteroatomic PNP ligands were made by reacting amines and phosphine chlorides $R_2PCl$ as described in (a) Ewart et al, *J. Chem. Soc.* 1964, 1543; (b) Dossett, S. J. et al, *Chem. Commun.*, 2001, 8, 699; (c) Balakrishna, M. S. et al., *J. Organomet. Chem.* 1990, 390, 2, 203). The respective phosphine chlorides $R_2PCl$ were prepared as described in literature (Casalnuovo, A. L. et al, *J. Am. Chem. Soc.* 1994, 116, 22, 9869; Rajanbabu, T. V. et al, *J. Org. Chem.* 1997, 62, 17, 6012). The (phenyl)$_2$PN(methyl)N(methyl)P(phenyl)$_2$ ligand was prepared according to Slawin et al. (Slawin, A. M. Z et al, *J. Chem. Soc., Dalton Trans.* 2002, 513). For the (phenyl)$_2$PN(SiMe$_3$)P(phenyl)$_2$ ligand the preparation method of Schmidbaur et al. was used (Schmidbaur, H. et al, *J. Organomet Chem.* 1984, 271, 173). The ligands (phenyl)$_2$P(=E)N($^i$propyl)P(phenyl)$_2$ with E=S, Se were prepared as described in Balakrishna, M. S. et al., *Inorg. Chem.* 1993, 32, 5676.

Example 1

Preparation of the (phenyl)$_2$PN(isopropyl)P(phenyl)$_2$ ligand

Example 1a)

Preparation of N,N-diisopropylphosphoramide dichloride

Diisopropylamine (70 ml, 0.50 mol) in toluene (80 ml) was added to a solution of PCl$_3$ (21.87 ml, 0.25 mol) in toluene (80 ml) at −10° C. The mixture was stirred for two hours and then allowed to warm to room temperature. The solution was stirred for a further hour after which it was filtered through a pad of celite. The product (35 g, 0.17 mol, 68%) was obtained after removal of the solvent. $^{31}P$ {H} NMR: 170 ppm

Example 1b)

Preparation of phenyl-magnesium bromide

Magnesium turnings (9.11 g, 0.375 mol) were treated with 4-bromobenzene (7.90 ml, 75 mmol) in THF (100 ml). A vigorous reaction ensued which was cooled in an ice bath. Once the reaction had dissipated, the reaction mixture was heated under reflux for 2 hours yielding the Grignard reagent.

Example 1c)

Preparation of Bis(phenyl)phosphorus chloride

The Grignard reagent was added to N,N-diisopropylphosphoramide dichloride (6.64 ml, 36 mmol) in THF (100 ml) at 0° C. After stirring at room temperature overnight the mixture was diluted with cyclohexane (200 ml) and dry HCl gas was bubbled through the solution for 0.5 hours. After filtration of the precipitate, the solvent was removed to give a mixture of the phosphine chloride and bromide in an 80% yield. This crude product was not isolated and all was used in the next step.

Example 1d)

Preparation of the (phenyl)$_2$PN(isopropyl)P(phenyl)$_2$ ligand

To a solution of the crude Bis(phenyl) phosphorus chloride (28.8 mmol calculated from crude reaction mixture) in DCM (80 ml) and triethylamine (15 ml) at 0° C. was added isopropylamine (1.11 ml, 13 mmol). The reaction was stirred for 30 min after which the ice bath was removed. After stirring for a total of 14 hrs the solution was filtered to remove the triethylammonium salt formed. The product was isolated after crystallisation in a 90% yield. $^{31}P$ {H} NMR: 49.0 ppm (broad singlet).

Example 2

Ethylene Tetramerisation Reaction Using CrCl$_3$(tetrahydrofuran)$_3$, (phenyl)$_2$PN(methyl)P(phenyl)$_2$ and MAO A solution of 29.0 mg of (phenyl)$_2$PN(methyl)P(phenyl)$_2$ (0.073 mmol) in 5 ml of toluene was added to a solution of 12.4 mg CrCl$_3$(tetrahydrofuran)$_3$ (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 80° C. The pressure reactor was charged with ethylene after which the reactor temperature was controlled at 85° C., while the ethylene pressure was maintained at 30 barg. Thorough mixing was ensured throughout by mixing speeds of 1100 RPM's using a gas entraining stirrer. The reaction was terminated after 60 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid products. These solid products were dried overnight in an oven at 100° C. and then weighed. The mass of total product was 31.86 g. The product distribution of this example is summarised in Table 1.

Example 3

Ethylene Tetramerisation Reaction Using $CrCl_3(tetrahydrofuran)_3$, $(phenyl)_2PN(methyl)P(phenyl)_2$ and MAO A solution of 22.4 mg of $(phenyl)_2PN(methyl)P(phenyl)_2$ (0.056 mmol) in 5 ml of toluene was added to a solution of 12.4 mg $CrCl_3(tetrahydrofuran)_3$ (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 80° C. The pressure reactor was charged with ethylene after which the reactor temperature was controlled at 85° C., while the ethylene pressure was maintained at 30 barg. The reaction was terminated after 60 min, and the procedure of Example 2 above was employed. The product mass was 28.76 g. The product distribution of this example is summarised in Table 1.

Example 4

Ethylene Tetramerisation Reaction Using $CrCl_3(tetrahydrofuran)_3$, $(phenyl)_2PN(methyl)P(phenyl)_2$ and MAO A solution of 26.3 mg of $(phenyl)_2PN(methyl)P(phenyl)_2$ (0.066 mmol) in 3 ml of toluene was added to a solution of 12.4 mg $CrCl_3(tetrahydrofuran)_3$ (0.033 mmol) in 17 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 30 barg. The reaction was terminated after 60 min, and the procedure of Example 2 above was employed. The product mass was 47.23 g. The product distribution of this example is summarised in Table 1.

Example 5

Ethylene Tetramerisation Reaction Using $CrCl_3(tetrahydrofuran)_3$, $(phenyl)_2PN(pentyl)P(phenyl)_2$ and MAO A solution of 30.0 mg of $(phenyl)_2PN(pentyl)P(phenyl)_2$ (0.074 mmol) in 10 ml of toluene was added to a solution of 12.4 mg $CrCl_3(tetrahydrofuran)_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 10.6 mmol) at 60° C. The pressure reactor was charged with ethylene after which the reactor temperature was controlled at 65° C., while the ethylene pressure was maintained at 30 barg. The reaction was terminated after 60 min, and the procedure of Example 2 above was employed. The product mass was 74.84 g. The product distribution of this example is summarised in Table 1.

Example 6

Ethylene Tetramerisation Reaction Using $CrCl_3(tetrahydrofuran)_3$, $(phenyl)_2PN(benzyl)P(phenyl)_2$ and MAO A solution of 30.7 mg of $(phenyl)_2PN(benzyl)P(phenyl)_2$ (0.065 mmol) in 10 ml of toluene was added to a solution of 12.4 mg $CrCl_3(tetrahydrofuran)_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 10.6 mmol) at 60° C. The pressure reactor was charged with ethylene after which the reactor temperature was controlled at 65° C., while the ethylene pressure was maintained at 30 barg. The reaction was terminated after 180 min, and the procedure of Example 2 above was employed. The product mass was 22.08 g. The product distribution of this example is summarised in Table 1.

Example 7

Ethylene Tetramerisation Reaction Using $CrCl_3(tetrahydrofuran)_3$, $(phenyl)_2PN(phenyl)P(phenyl)_2$ and MAO A solution of 34.9 mg of $(phenyl)_2PN(phenyl)P(phenyl)_2$ (0.076 mmol) in 10 ml of toluene was added to a solution of 13.5 mg $CrCl_3(tetrahydrofuran)_3$ (0.036 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 10.6 mmol) at 60° C. The pressure reactor was charged with ethylene after which the reactor temperature was controlled at 65° C., while the ethylene pressure was maintained at 30 barg. The reaction was terminated after 180 min, and the procedure of Example 2 above was employed. The product mass was 48.21 g. The product distribution of this example is summarised in Table 1.

Example 8

Ethylene Tetramerisation Reaction Using $CrCl_3(tetrahydrofuran)_3$, $(phenyl)_2PN(p-methoxy-phenyl)P(phenyl)_2$ and MAO A solution of 30.6 mg of $(phenyl)_2PN(p-methoxyphenyl)P(phenyl)_2$ (0.062 mmol) in 10 ml of toluene was added to a solution of 12.4 mg $CrCl_3(tetrahydrofuran)_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 10.6 mmol) at 60° C. The pressure reactor was charged with ethylene after which the reactor temperature was controlled at 65° C., while the ethylene pressure was maintained at 30 barg. The reaction was terminated after 60 min, and the procedure of Example 2 above was employed. The product mass was 7.01 g. The product distribution of this example is summarised in Table 1.

Example 9

Ethylene Tetramerisation Reaction Using CrCl$_3$(tetrahydrofuran)$_3$, (phenyl)$_2$PN(p-$^t$butylphenyl)P(phenyl)$_2$ and MAO A solution of 29.3 mg of (phenyl)$_2$PN(p-$^t$butylphenyl)P(phenyl)$_2$ (0.062 mmol) in 10 ml of toluene was added to a solution of 12.4 mg CrCl$_3$(tetrahydrofuran)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 10.6 mmol) at 60° C. The pressure reactor was charged with ethylene after which the reactor temperature was controlled at 65° C., while the ethylene pressure was maintained at 30 barg. The reaction was terminated after 180 min, and the procedure of Example 2 above was employed. The product mass was 62.15 g. The product distribution of this example is summarised in Table 1.

Example 10

Ethylene Tetramerisation Reaction Using Cr(2-ethylhexanoate)$_3$, (phenyl)$_2$PN(allyl)P(phenyl)$_2$ and MAO A solution of 27.6 mg of (phenyl)$_2$PN(allyl)P(phenyl)$_2$ (0.066 mmol) in 10 ml of toluene was added to a solution of 22.8 mg Cr(2-ethylhexanoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 30 barg. The reaction was terminated after 30 min, and the procedure of Example 2 above was employed. The product mass was 12.68 g. The product distribution of this example is summarised in Table 1.

Example 11

Ethylene Tetramerisation Reaction Using Cr(acetylacetonoate)$_3$, (phenyl)$_2$PN[(CH$_2$)$_3$Si(OMe)$_3$]P(phenyl)$_2$ and MAO A solution of 36.1 mg of (phenyl)$_2$PN[(CH$_2$)$_3$Si(OMe)$_3$]P(phenyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 60° C. The pressure reactor was charged with ethylene after which the reactor temperature was controlled at 65° C., while the ethylene pressure was maintained at 30 barg. The reaction was terminated after 30 min, and the procedure of Example 2 above was employed. The product mass was 72.96 g. The product distribution of this example is summarised in Table 1.

Example 12

Ethylene Tetramerisation Reaction Using Cr(acetylacetonoate)$_3$, (phenyl)$_2$PN[(CH$_2$)$_3$—N-morpholine]P(phenyl)$_2$ and MAO A solution of 33.8 mg of (phenyl)$_2$PN[(CH$_2$)$_3$—N-morpholine]P(phenyl)$_2$ (0.066 mmol) in 10 ml of toluene was added to a solution of 11.5 mg Cr(acetylactonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 30 barg. The reaction was terminated after 30 min, and the procedure of Example 2 above was employed. The product mass was 22.2 g. The product distribution of this example is summarised in Table 1.

Example 13

Ethylene Tetramerisation Reaction Using CrCl$_3$(tetrahydrofuran)$_3$, (phenyl)$_2$PN($^i$propyl)P(phenyl)$_2$ and MAO A solution of 26.1 mg of (phenyl)$_2$PN($^i$propyl)P(phenyl)$_2$ (0.061 mmol) in 10 ml of toluene was added to a solution of 11.6 mg CrCl$_3$(tetrahydrofuran)$_3$ (0.031 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 10.6 mmol) at 60° C. The pressure reactor was charged with ethylene after which the reactor temperature was controlled at 65° C., while the ethylene pressure was maintained at 30 barg. The reaction was terminated after 180 min, and the procedure of Example 2 above was employed. The product mass was 56.44 g. The product distribution of this example is summarised in Table 1.

Example 14

Ethylene Tetramerisation Reaction Using CrCl$_3$(tetrahydrofuran)$_3$, (phenyl)$_2$PN($^i$propyl)P(phenyl)$_2$ and MAO A solution of 17.1 mg of (phenyl)$_2$PN($^i$propyl)P(phenyl)$_2$ (0.04 mmol) in 10 ml of toluene was added to a solution of 7.5 mg CrCl$_3$(tetrahydrofuran)$_3$ (0.02 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.0 mmol) at 40° C. The pressure reactor was charged with ethylene after which the reactor temperature was maintained at 43° C., while the ethylene pressure was kept at 45 barg. The reaction was terminated after 60 min, and the procedure of Example 2 above was employed. The product mass was 39.98 g. The product distribution of this example is summarised in Table 1.

Example 15

Ethylene Tetramerisation Reaction Using Cr(2-ethylhexanoate)$_3$, (phenyl)$_2$PN($^i$propyl)P(phenyl)$_2$ and MAO A solution of 18.8 mg of (phenyl)$_2$PN($^i$propyl)P(phenyl)$_2$ (0.022 mmol) in 10 ml of toluene was added to a solution of 7.6 mg Cr(2-ethylhexanoate)$_3$ (0.011 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 3.3 mmol) at 40° C. The pressure reactor was charged with ethylene after which the reactor temperature was controlled at 45° C., while the ethylene pressure was maintained at 45 barg. The reaction was terminated after 50 min, and the procedure of Example 2 above was employed. The product mass was 64.71 g. The product distribution of this example is summarised in Table 1.

Example 16

Ethylene Tetramerisation Reaction Using Cr(acetylacetonoate)$_3$, (phenyl)$_2$PN($^i$propyl)P(phenyl)$_2$ and MAO A solution of 28.2 mg of (phenyl)$_2$PN($^i$propyl)P(phenyl)$_2$ (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 14 min, and the procedure of Example 2 above was employed. The product mass was 75.80 g. The product distribution of this example is summarised in Table 1.

Example 17

Ethylene Tetramerisation Reaction Using Cr(acetylacetonoate)$_3$, (phenyl)$_2$PN($^i$propyl)P(phenyl)$_2$ and EAO/TMA A solution of 28.2 mg of (phenyl)$_2$PN($^i$propyl)P(phenyl)$_2$ (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml), EAO (ethylaluminoxane, 33 mmol) and TMA (trimethylaluminum, 8.3 mmol) at 40° C. The pressure reactor was charged with ethylene after which the reactor temperature was controlled at 45° C., while the ethylene pressure was maintained at 45 barg. The reaction was terminated after 37 min, and the procedure of Example 2 above was employed. The product mass was 29.03 g. The product distribution of this example is summarised in Table 1.

Example 18

Ethylene Tetramerisation Reaction Using Cr(acetylacetonoate)$_3$, (phenyl)$_2$PN($^i$propyl)P(phenyl)$_2$ and MMAO A solution of 17.1 mg of (phenyl)$_2$PN($^i$propyl)P(phenyl)$_2$ (0.04 mmol) in 10 ml of toluene was added to a solution of 7.0 mg Cr(acetylacetonoate)$_3$ (0.02 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (modified methylaluminoxane, Akzo Nobel MMAO-3A, 6.0 mmol) at 40° C. The pressure reactor was charged with ethylene after which the reactor temperature was controlled at 45° C., while the ethylene pressure was maintained at 45 barg. The reaction was terminated after 15 min, and the procedure of Example 2 above was employed. The product mass was 74.11 g. The product distribution of this example is summarised in Table 1.

Example 19

Ethylene Tetramerisation Reaction Using Cr(acetylactonate)$_3$, (phenyl)$_2$PN($^i$propyl)P(phenyl)$_2$ and supported MAO A solution of 28.2 mg of (phenyl)$_2$PN($^i$propyl)P(phenyl)$_2$ (0.066 mmol) in 10 ml of toluene was added to a solution of 11.5 mg Cr( )$_3$ (0.033 mmol) in 10 ml toluene in a Schlenk vessel. The mixture was stirred for 5 min at ambient temperature. 3.9 g supported MAO (MAO on SiO$_2$, Crompton, containing 11.3 mmol MAO) was suspended in 30 ml of toluene and was then transferred to a 300 ml pressure reactor (autoclave) containing a mixture of toluene (50 ml) and TMA (trimethylaluminum, 3.3 mmol) at 40° C. The catalyst solution was then added to the pressure reactor. The pressure reactor was charged with ethylene after which the reactor temperature was controlled at 45° C., while the ethylene pressure was maintained at 45 barg. The reaction was terminated after 15 min, and the procedure of Example 2 above was employed. The product mass was 43.61 g. The product distribution of this example is summarizsed in Table 1.

Example 20

Ethylene Tetramerisation Reaction using Cr(acetylacetonoate)$_3$, (phenyl)$_2$PN($^i$propyl)P(phenyl)$_2$ and MAO A solution of 18.8 mg of (phenyl)$_2$PN($^i$propyl)P(phenyl)$_2$ (0.044 mmol) in 6.4 ml of cumene was added to a solution of 7.7 mg Cr(acetylacetonoate)$_3$ (0.022 mmol) in 8 ml cumene in a Schlenk vessel. The mixture was stirred for 5 min at ambient temperature and was then transferred to a 1000 ml pressure reactor (autoclave) containing a mixture of cumene (180 ml) and MAO (methylaluminoxane, 4.4 mmol, 10% solution in toluene) at 40° C. The pressure reactor was charged with ethylene after which the reactor temperature was controlled at 45° C., while the ethylene pressure was maintained at 45 barg. The reaction was terminated after 25 min, and the procedure of Example 2 above was employed. The product mass was 118.78 g. The product distribution of this example is summarised in Table 1.

Example 21

Ethylene Tetramerisation Reaction Using Cr(acetylacetonoate)$_3$, (phenyl)$_2$PN($^i$propyl)P(phenyl)$_2$ and MAO A solution of 11.1 mg of (phenyl)$_2$PN($^i$propyl)P(phenyl)$_2$ (0.026 mmol) in 10 ml of ethylbenzene was added to a solution of 7.0 mg Cr(acetylacetonoate)$_3$ (0.02 mmol) in 10 ml ethylbenzene in a Schlenk vessel. The mixture was stirred for 5 min at ambient temperature and was then transferred to a 300 ml pressure reactor (autoclave) containing a mixture of ethylbenzene (76 ml) and MAO (methylaluminoxane, 4.0 mmol, 7% solution in toluene) at 40° C. The pressure reactor was charged with ethylene after which the reactor temperature was controlled at 45° C., while the ethylene pressure was maintained at 45 barg. The reaction was terminated after 10 min, and the procedure of Example 2 above was employed.

The product mass was 70.6 g. The product distribution of this example is summarised in Table 1.

Example 22

Ethylene Tetramerisation Reaction Using Cr(acetylacetonoate)$_3$, (phenyl)$_2$PN($^i$propyl)P(phenyl)$_2$ and MAO A solution of 5.8 mg of (phenyl)$_2$PN($^i$propyl)P(phenyl)$_2$ (0.014 mmol) in 10 ml of cyclohexane was added to a solution of 3.5 mg Cr(acetylacetonoate)$_3$ (0.01 mmol) in 10 ml cyclohexane in a Schlenk vessel. The mixture was stirred for 5 min at ambient temperature. This solution and a solution of MAO (methylaluminoxane, 2.0 mmol, 7% solution in toluene) was added via a burette to a 1000 ml pressure reactor (autoclave) containing cyclohexane (170 ml) at 45° C. and being pressurised at 40 bar. After the addition, the ethylene pressure was maintained at 45 barg and the temperature controlled at 45° C. The reaction was terminated after 39 min, and the procedure of Example 2 above was employed. The product mass was 307.30 g. The product distribution of this example is summarized in Table 1.

Example 23

Ethylene Tetramerisation Reaction Using Cr(acetylacetonoate)$_3$, (phenyl)$_2$PN($^i$propyl)P(phenyl)$_2$ and MAO A solution of 11.6 mg of (phenyl)$_2$PN($^i$propyl)P(phenyl)$_2$ (0.026 mmol) in 10 ml of cumene was added to a solution of 7.4 mg Cr(acetylacetonoate)$_3$ (0.02 mmol) in 10 ml cumene in a Schlenk vessel. The mixture was stirred for 5 min at ambient temperature. This solution and a solution of MAO (methylaluminoxane, 2.8 mmol, 7% solution in toluene) was added via a burette to a 1000 ml pressure reactor (autoclave) containing cumene (180 ml) at 45° C. and being pressurised at 40 bar. After the addition, the ethylene pressure was maintained at 45 barg and the temperature controlled at 45° C. The reaction was terminated after 75 min, and the procedure of Example 2 above was employed. The product mass was 308.83 g. The product distribution of this example is summarised in Table 1.

Example 24

Ethylene Tetramerisation Reaction Using Cr(acetylacetonoate)$_3$, (2-naphthyl)$_2$PN(methyl)P(2-naphthyl)$_2$ and MAO A solution of 39.6 mg of (2-naphthyl)$_2$PN(methyl)P(2-naphthyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 60° C. The pressure reactor was charged with ethylene after which the reactor temperature was maintained at 65° C., while the ethylene pressure was kept at 30 barg. The reaction was terminated after 30 min, and the procedure of Example 2 above was employed. The product mass was 45.18 g. The product distribution of this example is summarised in Table 1.

Example 25

Ethylene Tetramerisation Reaction Using Cr(acetylacetonoate)$_3$, (p-biphenyl)$_2$PN(methyl)P(p-biphenyl)$_2$ and MAO A solution of 47.0 mg of (p-biphenyl)$_2$PN(methyl)P(p-biphenyl)$_2$ (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 30 barg. The reaction was terminated after 30 min, and the procedure of Example 2 above was employed. The product mass was 26.41 g. The product distribution of this example is summarised in Table 1.

Example 26

Ethylene Tetramerisation Reaction Using Cr(acetylacetonoate)$_3$, (m-methylphenyl)$_2$PN(methyl)P(m-methylphenyl)$_2$ and MAO A solution of 30.1 mg of (m-methylphenyl)$_2$PN(methyl)P(m-methylphenyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 60° C. The pressure reactor was charged with ethylene after which the reactor temperature was controlled at 45° C., while the ethylene pressure was maintained at 65 barg. The reaction was terminated after 30 min, and the procedure of Example 2 above was employed. The product mass was 52.34 g. The product distribution of this example is summarised in Table 1.

Example 27

Ethylene Tetramerisation Reaction Using Cr(acetylacetonoate)$_3$, (p-methylphenyl)$_2$PN(methyl)P(p-methylphenyl)$_2$ and MAO A solution of 30.1 mg of (p-methylphenyl)$_2$PN(methyl)P(p-methylphenyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 60° C. The pressure reactor was charged with ethylene after which the reactor temperature was maintained at 65° C., while the ethylene pressure was kept at 45 barg. The reaction was terminated after 15 min, and the procedure of Example 2 above was employed. The product mass was 80.59 g. The product distribution of this example is summarised in Table 1.

Example 28

Ethylene Tetramerisation Reaction Using Cr(acetylacetonoate)$_3$, (o-ethylphenyl)(Ph)PN($^i$propyl)PPh$_2$ and MAO

A solution of 30.1 mg of (o-ethylphenyl)(Ph)PN($^i$propyl)PPh$_2$ (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 14 min, and the procedure of Example 2 above was employed. The product mass was 63.78 g. The product distribution of this example is summarised in Table 1.

Example 29

Ethylene Tetramerisation Reaction Using Cr(acetylacetonoate)$_3$, (phenyl)$_2$P(=S)N($^i$propyl)P(phenyl)$_2$ and MAO

A solution of 30.3 mg of (phenyl)$_2$P(=S)N($^i$propyl)P(phenyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 30 min, and the procedure of Example 2 above was employed. The product mass was 33.06 g. The product distribution of this example is summarised in Table 1.

Example 30

Ethylene Tetramerisation Reaction Using Cr(acetylacetonoate)$_3$, (phenyl)$_2$PN($^i$propyl)P(phenyl)$_2$ and MAO

A solution of 11.6 mg of (phenyl)$_2$PN($^i$propyl)P(phenyl)$_2$ (0.026 mmol) in 10 ml of cumene was added to a solution of 7.4 mg Cr(acetylacetonoate)$_3$ (0.02 mmol) in 10 ml cumene in a Schlenk vessel. The mixture was stirred for 5 min at ambient temperature. This solution and a solution of MAO (methylaluminoxane, 4.0 mmol, 7% solution in toluene) was added via a burette to a 1000 ml pressure reactor (autoclave) containing a mixture of cumene (80 ml) and 1-octene (80 ml) at 45° C. and being pressurised at 40 bar. After the addition, the ethylene pressure was maintained at 45 barg and the temperature controlled at 45° C. The reaction was terminated after 45 min, and the procedure of Example 2 above was employed. The product mass was 405.87 g. The product distribution of this example is summarised in Table 1.

Example 31

Ethylene Tetramerisation Reaction Using Cr(acetylacetonoate)$_3$, (phenyl)$_2$PN(methyl)N(methyl)P(phenyl)$_2$ and MAO

A solution of 28.3 mg of (phenyl)$_2$PN(methyl)N(methyl)P(phenyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 30 min, and the procedure of Example 2 above was employed. The liquid product mass was 22.45 g. The product distribution of this example is summarised in Table 1.

Example 32

Ethylene Tetramerisation Reaction Using Cr(acetylacetonoate)$_3$, (2-thiophenyl)$_2$PN(methyl)P(2-thiophenyl)$_2$ and MAO

A solution of 37.2 mg of (2-thiophenyl)$_2$PN(methyl)P(2-thiophenyl)$_2$ (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 30 min, and the procedure of Example 2 above was employed. The product mass was 14.7 g. The product distribution of this example is summarised in Table 1.

Example 33

Ethylene Tetramerisation Reaction Using Cr(acetylacetonoate)$_3$, (phenyl)$_2$PN($^i$propyl)P(phenyl)$_2$ and MAO

A solution of 5.8 mg of (phenyl)$_2$PN($^i$propyl)P(phenyl)$_2$ (0.015 mmol) in 10 ml of cyclohexane was added to a solution of 3.8 mg Cr(acetylacetonoate)$_3$ (0.011 mmol) in 10 ml cyclohexane in a Schlenk vessel. The mixture was stirred for 5 min at ambient temperature. 1.8 mmol of MAO (methylaluminoxane, 7% solution in toluene) was added and the mixture was stirred for 5 min. This solution was added via a burette to a 1000 ml pressure reactor (autoclave) containing cyclohexane (180 ml) at 45° C. and being pressurised at 40 bar. After the addition, the ethylene pressure was maintained at 45 barg and the temperature controlled at 45° C. The reaction was terminated after 60 min, and the procedure of Example 2 above was employed. The product mass was 297.69 g. The product distribution of this example is summarised in Table 1.

Example 34

Ethylene Tetramerisation Reaction Using Cr(acetylacetonoate)$_3$, (phenyl)$_2$PN(SiMe$_3$)P(phenyl)$_2$ and MAO A solution of 39.8 mg of (phenyl)$_2$PN(SiMe$_3$)P(phenyl)$_2$ (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 30 min, and the procedure of Example 2 above was employed. The product mass was 26.9 g. The product distribution of this example is summarised in Table 1.

Example 35

Ethylene Tetramerisation Reaction Using Cr(acetylacetonoate)$_3$, [(phenyl$_2$P)$_2$NCH$_2$CH$_2$]N and MAO A solution of 62.5 mg of [(phenyl$_2$P)$_2$NCH$_2$CH$_2$]N (0.066 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 30 barg. The reaction was terminated after 30 min, and the procedure of Example 2 above was employed. The product mass was 2.5 g. The product distribution of this example is summarised in Table 1.

Example 36

Ethylene Tetramerisation Reaction Using Cr(acetylacetonoate)$_3$, (o-methylphenyl)$_2$PN($^i$propyl)P(o-methylphenyl)(phenyl) and MAO A solution of 11.7 mg of (o-methylphenyl)$_2$PN($^i$propyl)P(o-methylphenyl)(phenyl) (0.026 mmol) in 10 ml of toluene was added to a solution of 7.7 mg Cr(acetylacetonoate)$_3$ (0.022 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 6.6 mmol) at 40° C. The pressure reactor was charged with ethylene after which the reactor temperature was controlled at 45° C., while the ethylene pressure was maintained at 45 barg. The reaction was terminated after 30 min, and the procedure of Example 2 above was employed. The product mass was 55.45 g. The product distribution of this example is summarised in Table 1.

Example 37

Figure 1:
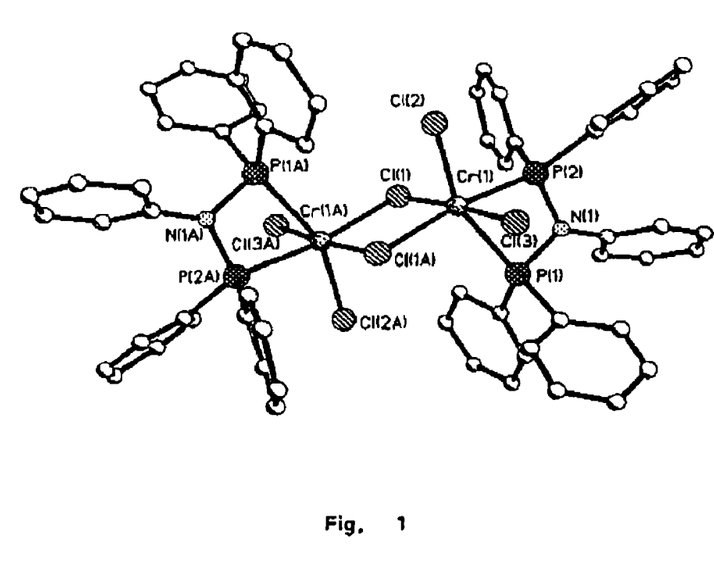
FIG. 1 shows the structure of a complex obtained by single crystal X-Ray analysis.

Preparation of [Cr{(phenyl)$_2$PN(phenyl)P(phenyl)$_2$}Cl$_2$(μ-Cl)]$_2$ (phenyl)$_2$PN(phenyl)P(phenyl)$_2$ (0.273 g, 0.591 mmol) and CrCl$_3$(thf)$_3$ (0.206 g, 0.550 mmol) were taken up in toluene (25 ml) and heated to 80° C. overnight, resulting in the precipitation of a blue powder. After cooling to room temperature, the toluene was filtered from the precipitate and the product washed twice with petroleum ether (10 ml). Drying under vacuum yielded 0.303 g (89%). Calculated for C$_{60}$H$_{50}$N$_2$P$_4$Cr$_2$Cl$_6$ (found): C, 58.13 (57.98); H, 4.07 (3.97); N, 2.26 (2.12) %. Magnetic moment 4.06 BM per Cr (5.74 BM per dimer). FIG. 1 shows the structure of the complex as obtained by single crystal X-ray analysis.

Example 38

Ethylene Tetramerisation Reaction Using [Cr{(phenyl)$_2$PN(phenyl)P(phenyl)$_2$}Cl$_2$(μ-Cl)]$_2$ and MAO A suspension of [Cr{(phenyl)$_2$PN(phenyl)P(phenyl)$_2$}Cl$_2$(μ-Cl)]$_2$ (0.0125 g, 0.020 mmol of Cr) in 20 ml of toluene was transferred to a 300 ml pressure reactor (autoclave) containing toluene (100 ml) and MAO (6.0 mmol) at 45° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 4.61 g. The product distribution of this example is summarised in Table 1.

Example 39

Preparation of the (ethyl)$_2$PN(methyl)P(ethyl)$_2$ ligand

Methylamine (3.1 ml of 2M solution, 6.2 mmol) in toluene (25 ml) was added slowly to a solution of chlorodiethylphosphine (1.582 g, 12.7 mmol) in toluene (15 ml) and triethylamine (5 ml). The mixture was stirred overnight before being filtered through a glass fibre filter. The solvents were removed under vacuum and 10 ml of water was added. The product was extracted in petroleum ether (3×5 ml) and organics combined. Removal of the solvent under vacuum yielded 1.046 g (81%) of the product. $^{31}$P{H} NMR: 68 ppm.

Example 40

Ethylene Tetramerisation Reaction Using Cr(2-ethylhexanoate)$_3$, (ethyl)$_2$PN(methyl)P(ethyl)$_2$ and MAO A solution of Cr(2-ethylhexanoate)$_3$ (0.002M in toluene, 10 ml, 0.020 mmol) and a solution of (ethyl)$_2$PN(methyl)P(ethyl)$_2$ (0.005M in toluene, 4.1 ml, 0.0205 mmol) were added to a 300 ml pressure reactor (autoclave) containing toluene (100 ml) and MAO (6.0 mmol) at 45° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 2.26 g. The product distribution of this example is summarised in Table 1.

Example 41

Preparation of [Cr{(ethyl)$_2$PN(methyl)P(ethyl)$_2$}Cl$_2$(μ-Cl)]$_2$

The procedure of example 38 was followed using (ethyl)$_2$PN(methyl)P(ethyl)$_2$ (0.362 g, 1.75 mmol) and CrCl$_3$(thf)$_3$ (0.594 g, 1.58 mmol). A yield of 0.520 g (90%) was obtained.

Calculated for $C_{18}H_{46}N_2P_4Cr_2Cl_6$ (found): C, 29.57 (29.62); H, 6.34 (6.45); N, 3.83 (3.87) %. Magnetic moment 3.86 BM per Cr (5.46 BM per dimer).

Example 42

Ethylene Tetramerisation Reaction Using [Cr{(ethyl)$_2$PN(methyl)P(ethyl)$_2$}Cl$_2$(µ-Cl)]$_2$ and MAO A suspension of Cr{(ethyl)$_2$PN(methyl)P(ethyl)$_2$}Cl$_2$(µ-Cl)]$_2$ (0.0075 g, 0.020 mmol of Cr) in 10 ml of toluene was transferred to a 300 ml pressure reactor (autoclave) containing toluene (100 ml) and MAO (6.0 mmol) at 45° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 3.06 g. The product distribution of this example is summarised in Table 1.

Example 43

Preparation of the (ethyl)$_2$PN(isopropyl)P(phenyl)$_2$ ligand

N-(diphenylphosphino)methylamine (1.870 g, 7.69 mmol) in toluene (15 ml) was slowly added to a solution of chlorodiethylphosphine (0.986, 7.92 mmol) in toluene (20 ml) and triethylamine (5 ml). The mixture was stirred overnight before being filtered through a glass fibre filter. The solvents were removed under vacuum and 10 ml of water was added. The product was extracted in petroleum ether (3×5 ml) and organics combined. Removal of the solvent under vacuum yielded 2.200 g (86%) of the product. $^{31}$P {H} NMR: 49, 43 ppm.

Example 44

Ethylene Tetramerisation Reaction Using Cr(2-ethylhexanoate)$_3$, (phenyl)$_2$PN(isopropyl)P(ethyl)$_2$ and MAO A solution of Cr(2-ethylhexanoate)$_3$ (0.002M in toluene, 10 ml, 0.020 mmol) and a solution of (phenyl)$_2$PN(isopropyl)P(ethyl)$_2$ (0.004M in toluene, 5 ml, 0.020 mmol) were added to a 300 ml pressure reactor (autoclave) containing toluene (100 ml) and MAO (6.0 mmol) at 45° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 10.83 g. The product distribution of this example is summarised in Table 1.

Example 45

Ethylene Tetramerisation Reaction Using Cr(2-ethylhexanoate)$_3$, (phenyl)(ethyl)PN(methyl)P(ethyl)(phenyl) and MAO A solution of Cr(2-ethylhexanoate)$_3$ (0.002M in toluene, 15 ml, 0.030 mmol) and a solution of (phenyl)(ethyl)PN(methyl)P(ethyl)(phenyl)(0.00365M in toluene, 9 ml, 0.033 mmol) were added to a 300 ml pressure reactor (autoclave) containing toluene (100 ml) and MAO (9.0 mmol) at 45° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 0.897 g. The product distribution of this example is summarised in Table 1.

Example 46

Ethylene Tetramerisation Reaction Using Cr(2-ethylhexanoate)$_3$, (phenyl)(ethyl)PN(isopropyl)P(phenyl)$_2$ and MAO A solution of Cr(2-ethylhexanoate)$_3$ (0.002M in toluene, 15 ml, 0.030 mmol) and a solution of (phenyl)(ethyl)PN(isopropyl)P(phenyl)(0.034 mmol in 9 ml toluene) were added to a 300 ml pressure reactor (autoclave) containing toluene (100 ml) and MAO (9.0 mmol) at 45° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 13.23 g. The product distribution of this example is summarised in Table 1.

Example 47

Ethylene Tetramerisation Reaction Using Cr(acetylacetonoate)$_3$, (phenyl)$_2$P(=Se)N($^i$propyl)P(phenyl)$_2$ and MAO A solution of 33.4 mg of (phenyl)$_2$P(=Se)N($^i$propyl)P(phenyl)$_2$ (0.066 mmol) in 15 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 40° C. The pressure reactor was charged with ethylene after which the reactor temperature was controlled at 45° C., while the ethylene pressure was maintained at 45 barg. The reaction was terminated after 30 min, and the procedure of Example 2 above was employed. The product mass was 8.45 g. The product distribution of this example is summarised in Table 1.

Example 48

Ethylene Tetramerisation Reaction Using Cr(acetylacetonoate)$_3$, (phenyl)$_2$PCH$_2$CH$_2$P(phenyl)$_2$ and MAO A solution of 26.3 mg of phenyl)$_2$PCH$_2$CH$_2$P(phenyl)$_2$ (0.198 mmol) in 10 ml of toluene was added to a solution of 11.5 mg Cr(acetylacetonoate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was controlled at 45° C., while the ethylene pressure was maintained at 40 barg. The reaction was terminated after 30 min, and the procedure of Example 2 above was employed. The product mass was 21.23 g. The product distribution of this example is summarised in Table 1.

TABLE 1

Ethylene tetramerisation runs: examples 2-48

| Example | activity g prod./g Cr | C-6 % of total product | C-8 % of total product | 1-oct. in C-8 % |
|---|---|---|---|---|
| 2 | 18600 | 42.3 | 53.6 | 96.0 |
| 3 | 16700 | 31.4 | 55.9 | 95.8 |
| 4 | 27400 | 23.9 | 56.5 | 93.9 |
| 5 | 43500 | 24.9 | 60.1 | 96.8 |
| 6 | 12800 | 28.0 | 60.2 | 98.1 |
| 7 | 25700 | 27.3 | 61.6 | 97.8 |
| 8 | 4080 | 26.4 | 52.8 | 97.8 |
| 9 | 36100 | 26.6 | 61.8 | 97.8 |
| 10 | 7400 | 22.2 | 53.6 | 96.6 |
| 11 | 42500 | 23.5 | 55.2 | 96.4 |
| 12 | 12900 | 19.2 | 45.4 | 96.4 |
| 13 | 35100 | 32.7 | 60.6 | 99.2 |
| 14 | 38400 | 23.9 | 69.0 | 99.0 |
| 15 | 113100 | 25.1 | 71.1 | 98.9 |
| 16 | 44200 | 19.1 | 67.9 | 99.0 |
| 17 | 16900 | 17.8 | 71.6 | 98.5 |
| 18 | 71300 | 16.0 | 70.7 | 97.9 |
| 19 | 25500 | 19.5 | 68.6 | 98.7 |
| 20 | 103800 | 25.1 | 72.0 | 99.0 |
| 21 | 64100 | 16.4 | 71.4 | 99.0 |
| 22 | 591000 | 14.1 | 67.4 | 98.7 |
| 23 | 297000 | 16.2 | 68.6 | 98.7 |
| 24 | 26300 | 26.0 | 54.2 | 93.4 |
| 25 | 15400 | 22.9 | 56.1 | 95.3 |
| 26 | 30500 | 20.0 | 57.0 | 95.3 |
| 27 | 47000 | 20.7 | 56.7 | 95.0 |
| 28 | 37200 | 27.1 | 63.4 | 98.0 |
| 29 | 19300 | 17.4 | 65.4 | 98.9 |
| 30 | 390300 | 15.5 | 65.2 | 98.8 |
| 31 | 13100 | 25.2 | 58.8 | 98.4 |
| 32 | 8600 | 16.6 | 60.3 | 96.6 |
| 33 | 572500 | 14.1 | 68.1 | 98.7 |
| 34 | 9030 | 18.8 | 52.5 | 95.7 |
| 35 | 1440 | 30.9 | 52.3 | 94.5 |
| 36 | 48500 | 41.5 | 41.8 | 98.4 |
| 38 | 4400 | 18.0 | 61.6 | 96.5 |
| 40 | 2200 | 16.8 | 45.2 | 97.4 |
| 42 | 2900 | 15.5 | 63.0 | 98.7 |
| 44 | 10400 | 20.2 | 69.0 | 99.6 |
| 45 | 580 | 13.3 | 42.1 | 97.1 |
| 46 | 8500 | 23.9 | 69.7 | 99.9 |
| 47 | 4900 | 13.2 | 45.1 | 98.0 |
| 48 | 12400 | 19.7 | 39.2 | 96.6 |

The invention claimed is:

1. A process for tetramerisation of olefins comprising contacting an olefinic feedstream with a catalyst system which includes the combination of
a transition metal compound;
a heteroatomic ligand described by the following general formula $(R)_n A-B-C(R)_m$ wherein
A and C are independently an atom selected from the group consisting of phosphorus, arsenic, antimony, oxygen, bismuth, sulphur, selenium and nitrogen or said atom oxidized by S, Se, N or O, where the valance of A and/or C allows for such oxidation;
B is a linking group between A and C;
the R groups are the same or different, and each R is independently selected from the group consisting of a hydrocarbyl group, a hetero hydrocarbyl group, a substituted hydrocarbyl group, and a substituted hetero hydrocarbyl group;
n and m for each R is independently determined by the respective valence and oxidation state of A and C; and provided that when the heteroatomic ligand is described by the following general formula $(R^1)(R^2)A-B-C(R^3)(R^4)$ wherein
A and C are independently selected from the group consisting of phosphorus, arsenic, antimony, bismuth and nitrogen;
B is a linking group between A and C; and
each of $R^1, R^2, R^3$ and $R^4$ is independently selected from the group consisting of a hydrocarbyl group, a hetero hydrocarbyl group, a substituted hydrocarbyl group, and a substituted hetero hydrocarbyl group,
any substituents that may be part of one or more of $R^1, R^2, R^3$ and $R^4$ are non electron donating and where $R^1, R^2, R^3$ and $R^4$ are independently aromatic, including hetero aromatic groups, not all the groups $R^1, R^2, R^3$ and $R^4$ have a substituent on the atom adjacent to the atom bound to A or C; and
an activator selected from the group consisting of organoaluminium compounds, organoboron compounds, organic salts, inorganic acids and salts, wherein the organoaluminium compounds are selected from the group of compounds of the formula $AlR_3$, where each R is independently a $C_1$-$C_{12}$ alkyl or a halide, aluminoxanes and modified aluminoxanes.

2. The process as claimed in claim 1, wherein the olefinic feedstream includes an α-olefin and the product stream includes at least 30% of a tetramerised α-olefin monomer.

3. The process as claimed in claim 1, wherein the olefinic feedstream includes ethylene and the product stream includes at least 30% 1-octene.

4. The process as claimed in claim 1, wherein the olefinic feedstream includes ethylene and wherein $(C_6+C_8):(C_4+C_{10})$ ratio in the product stream is more than 2.5:1.

5. The process as claimed in claim 3, wherein ethylene is contacted with the catalyst system at a pressure of more than 1000 kPa (10 barg).

6. The process as claimed in claim 1, wherein the heteroatomic ligand is described by the following general formula $(R^1)(R^2)A-B-C(R^3)(R^4)$; wherein A and C are independently selected from the group consisting of phosphorus, arsenic, antimony, bismuth and nitrogen; B is a linking group between A and C; and each of $R^1, R^2, R^3$ and $R^4$ is independently selected from the group consisting of a hydrocarbyl group, a hetero hydrocarbyl group, a substituted hydrocarbyl group, and a substituted hetero hydrocarbyl group.

7. The process as claimed in claim 6, wherein the heteroatomic ligand is described by the following general formula $(R^1)(R^2)A-B-C(R^3)(R^4)$; wherein A and C are independently selected from the group comprising of phosphorous, arsenic, antimony, bismuth and nitrogen; B is a linking group between A and C; and each of $R^1, R^2, R^3$ and $R^4$ is independently selected from the group consisting of a non-aromatic hydrocarbyl group, a non-aromatic heterohydrocarbyl group, an aromatic hydrocarbyl group, an aromatic heterohydrocarbyl group and a hetero aromatic heterohydrocarbyl group.

8. The process as claimed in claim 6, wherein each of $R^1, R^2, R^3$ and $R^4$ is independently an aromatic group, including a hetero aromatic group and not all the groups $R^1, R^2, R^3$ and $R^4$ have a substituent on the atom adjacent to the atom bound to A or C.

9. The process as claimed in claim 1, wherein each non electron donating substituent is non polar.

10. The process as claimed in claim 1, wherein B is selected from the group consisting of: an organic linking group comprising a hydrocarbylene, a substituted hydrocarbylene, a heterohydrocarbylene, or a substituted heterohydrocarbylene; an inorganic linking group comprising a single atom linking spacer; and a group comprising methylene, dimethylmethylene, 1,2-ethylene, 1,2-phenylene, 1,2-propylene, 1,2-catecholate, —(CH$_2$)N—N(CH$_3$)—, —B(R$^5$)-, —Si(R$^5$)$_2$, —P(R$^5$)— or —N(R$^5$)—, wherein R$^5$ is hydrogen, a hydrocarbyl or a substituted hydrocarbyl, a substituted heteroatom or a halogen.

11. The process as claimed in claim 10, wherein B is a single atom linking spacer.

12. The process as claimed in claim 10, wherein B is —N(R$^5$)—, wherein R$^5$ is selected from the group consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, a silyl group or a derivative thereof, and an aryl group substituted with any of these substituents.

13. The process as claimed claim 1, wherein A and/or C is independently oxidised by S, Se, N or O, where the valence of A and/or C allows for such oxidation.

14. The process as claimed in claim 1, wherein each of A and C is phosphorus.

15. The process as claimed in claim 12, wherein each of R$^1$, R$^2$, R$^3$ and R$^4$ is independently selected from the group consisting of benzyl, phenyl, tolyl, xylyl, mesityl, biphenyl, naphthyl, anthracenyl, dimethylamino, diethylamino, methylethylamino, thiophenyl, pyridyl, thioethyl, thiophenoxy, trimethylsilyl, dimethyihydrazyl, methyl, ethyl, ethenyl, propyl, butyl, propenyl, propynyl, cyclopentyl, cyclohexyl, ferrocenyl and tetrahydrofuranyl group.

16. The process as claimed in claim 15, wherein each of R$^1$, R$^2$, R$^3$ and R$^4$ is independently selected from the group consisting of a phenyl, tolyl, biphenyl, naphthyl, thiophenyl and ethyl group.

17. The process as claimed in claim 1, wherein the ligand is selected from the group consisting of
(phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$-PN(p-$^t$butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (ethyl)$_2$PN(methyl)P(ethyl)2, (ethyl)$_2$PN(isopropyl)P(phenyl)$_2$, (ethyl)(phenyl)PN(methyl)P(ethyl)(phenyl), (ethyl)(phenyl)PN(isopropyl)P(phenyl)$_2$, (phenyl)$_2$P(=Se)N(isopropyl)P(phenyl)$_2$, (phenyl)$_2$PCH$_2$CH$_2$P(phenyl)$_2$, (o-ethylphenyl)(phenyl)PN(isopropyl)P(phenyl)$_2$, (o-methylphenyl)$_2$PN(isopropyl)P(o-methylphenyl)(phenyl), (phenyl)$_2$PN(benzyl)P(phenyl)$_2$, (phenyl)$_2$PN(1-cyclohexyl-ethyl)P(phenyl)$_2$, (phenyl)$_2$PN[CH$_2$CH$_2$CH$_2$Si(OMe$_3$)]P(phenyl)$_2$, (phenyl)$_2$PN(cyclohexyl)P(phenyl)$_2$, (phenyl)$_2$PN(2-methylcyclohexyl)P(phenyl)$_2$, (phenyl)$_2$PN(allyl)P(phenyl)$_2$, (2-naphthyl)$_2$PN(methyl)P(2-naphthyl)$_2$, (p-biphenyl)$_2$-PN(methyl) P(p-biphenyl)$_2$, (p-methylphenyl)$_2$PN(methyl)P(p-methylphenyl)$_2$, (2-thiophenyl)$_2$PN(methyl)P(2-thiophenyl)$_2$, (phenyl)$_2$PN(methyl)N(methyl)P(phenyl)$_2$, (m-methylphenyl)$_2$PN(methyl )P(m-methylphenyl )$_2$, (phenyl)$_2$PN(isopropyl)P(phenyl)$_2$, and (phenyl)$_2$P(=S)N(isopropyl)P(phenyl)$_2$.

18. The process as claimed in claim 1, wherein the catalyst system is prepared by combining in any order the heteroatomic ligand, the transition metal compound and the activator.

19. The process as claimed in claim 1, wherein the catalyst system is a pre-formed coordination complex prepared by combining the heteroatomic ligand and the transition metal compound and wherein the pre-formed coordination complex is added to the olefinic feedstream and the activator.

20. The process as claimed in claim 1, wherein the transition metal in the transition metal compound is selected from the group consisting of chromium, molybdenum, tungsten, titanium, tantalum, vanadium and zirconium.

21. The process as claimed in claim 20, wherein the transition metal is chromium.

22. The process as claimed in claim 1, wherein the transition metal compound is selected from the group consisting of an inorganic salt, an organic salt, a co-ordination complex and organometallic complex.

23. The process as claimed in claim 22, wherein the transition metal compound is selected from the group consisting of chromium trichloride tris-tetrahydrofuran complex, (benzene)tricarbonyl chromium, chromium (III) octanoate, chromium (III) acetylacetonate, chromium hexacarbonyl and chromium (III)2-ethylhexanoate.

24. The process as claimed in claim 23, wherein the transition metal is a complex selected from chromium (III) acetylacetonate and chromium (III)2-ethylhexanoate.

25. The process as claimed in claim 1, wherein the transition metal compound and the heteroatomic ligand are combined to provide a transition metal/ligand ratio from about 0.01:100 to 10 000:1.

26. The process as claimed in claim wherein the activator is an alkylaluminoxane and the transition metal and the aluminoxane are combined in proportions to provide an Al/transition metal ratio from about 1:1 to 10 000:1.

27. A catalyst system which includes the combination of a chromium compound; and
a heteroatomic ligand described by the following general formula wherein
A and C are independently an atom selected from the group consisting of phosphorus, arsenic, antimony, bismuth, and nitrogen or said atom oxidized by S, Se, N or O, where the valance of A and/or C allows for such oxidation;
B is a linking group between A and C;
the R groups are the same or different, and each R is independently selected from the group consisting of a hydrocarbyl group, a heterohydrocarbyl group, a substituted hydrocarbyl group, and a substituted heterohydrocarbyl group; and
provided that when
A and C are independently selected from the group consisting of phosphorus, arsenic, antimony, bismuth and nitrogen;
B is a linking group between A and C and is selected from the group consisting of a hydrocarbylene, a substituted hydrocarbylene, an inorganic linking group comprising a single atom linking spacer and —(CH$_3$)N—N(CH$_3$)—, —B(R$^5$)—, —Si(R$^5$)$_2$, —P(R$^5$)— and —N(R$^5$)—, where R$^5$ is hydrogen, a hydrocarbyl or substituted hydrocarbyl, a substituted heteroatom or a halogen; and
each of R$^1$, R$^2$ R$^3$ and R$^4$ is independently selected from the group consisting of a hydrocarbyl group, a heterohydrocarbyl group, a substituted hydrocarbyl group, and a substituted heterohydrocarbyl group,
any substituents that may be part of one or more of R$^1$, R$^2$, R$^3$ and R$^4$ are non electron donating and where R$^1$, R$^2$, R$^3$ and R$^4$ are independently aromatic, including hetero aromatic groups, not all the groups R$^1$, R$^2$, R$^3$ and R$^4$ have a substituent on the atom adjacent to the atom bound to A or C.

28. The catalyst system of claim 27, wherein B is —N(R$^5$)—, wherein R$^5$ is selected from the group consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, a silyl group or a derivative thereof, and an aryl group substituted with any of these substituents.

29. The catalyst system of claim 27, wherein each of A and C is independently phosphorus.

30. The catalyst system of claim 27, wherein each of R$^1$, R$^2$, R$^3$ and R$^4$ is independently selected from the group consisting of benzyl, phenyl, tolyl, xylyl, mesityl, biphenyl, naphthyl, anthracenyl, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group.

31. The catalyst system of claim 30, wherein each of R$^1$, R$^2$, R$^3$ and R$^4$ are independently selected from the group consisting of a phenyl, tolyl, biphenyl, naphthyl, thiophenyl and ethyl group.

32. The catalyst system of claim 27, wherein the ligand is selected from the group consisting of (phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$-PN(p-$^t$butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (ethyl)$_2$PN(methyl)P(ethyl)2, (ethyl)$_2$PN(isopropyl)P(phenyl)$_2$, (ethyl)(phenyl)PN(methyl)P(ethyl)(phenyl), (ethyl)(phenyl)PN(isopropyl)P(phenyl)$_2$, (phenyl)$_2$P(=Se)N(isopropyl)P(phenyl)$_2$, (phenyl)$_2$PCH$_2$CH$_2$P(phenyl)2, (o-ethylphenyl)(phenyl)PN(isopropyl)P(phenyl)$_2$, (o-methylphenyl)$_2$PN(isopropyl)P(o-methylphenyl)(phenyl), (phenyl)$_2$PN(benzyl)P(phenyl)$_2$(phenyl)$_2$ PN(1-cyclohexyl-ethyl)P(phenyl)$_2$, (phenyl)$_2$PN[CH$_2$CH$_2$CH$_2$Si(OMe3)]P(phenyl)$_2$, (phenyl)$_2$PN(cyclohexyl)P(phenyl)$_2$(phenyl)$_2$PN(2-methylcyclohexyl)P(phenyl)$_2$, (phenyl)$_2$PN(allyl)P(phenyl)$_2$(2-naphthyl)$_2$PN(methyl)P($_2$-naphthyl)$_2$, (p-biphenyl)$_2$-PN(methyl)P(p-biphenyl)$_2$, (p-methylphenyl)$_2$PN(methyl)P(p-methylphenyl)$_2$, (2-thiophenyl)$_2$PN(methyl)P(2-thiophenyl)$_2$(phenyl)$_2$PN(methyl)N(methyl)P(phenyl)$_2$, (m-methylphenyl)$_2$PN(methyl)P(m-methylphenyl )$_2$, (phenyl)$_2$PN(isopropyl)P(phenyl)$_2$, and (phenyl)$_2$P(=S)N(isopropyl)P(phenyl)$_2$.

33. The catalyst system of claim 27, wherein the chromium compound is selected from the group consisting of an inorganic salt, organic salt, a co-ordination complex and organometallic complex.

34. The catalyst system of claim 33, wherein the chromium compound is selected from the group consisting of chromium trichloride tris-tetrahydrofuran complex, (benzene)tricarbonyl chromium, chromium (III) octanoate, chromium (III) acetylacetonoate, chromium hexacarbonyl and chromium (III) 2-ethyihexanoate.

35. The catalyst system of claim 27, wherein the chromium from the chromium compound and the heteroatomic ligand are combined to provide a chromium/ligand ratio from about 0.01:100 to 10 000:1.

36. The catalyst system of claim 27, which further includes an activator.

37. The catalyst system of claim 36, wherein the activator is an alkylaluminoxane.

38. The catalyst system of claim 37, wherein the chromium and the aluminoxane are combined in proportions to provide an Al/chromium ratio from about 1:1 to 10 000:1.

* * * * *